(12) United States Patent
Peters

(10) Patent No.: US 10,495,606 B2
(45) Date of Patent: Dec. 3, 2019

(54) PROBE DEVICE, ROTATING HEAD, AND TEST APPARATUS

(71) Applicant: Prüftechnik Dieter Busch AG, Ismaning (DE)

(72) Inventor: Jürgen Peters, Pliening (DE)

(73) Assignee: Prüftechnik Dieter Busch AG, Ismaning (DE)

( * ) Notice: Subject to any disclaimer, the term of this patent is extended or adjusted under 35 U.S.C. 154(b) by 0 days.

(21) Appl. No.: 15/747,712

(22) PCT Filed: Jul. 13, 2016

(86) PCT No.: PCT/DE2016/100312
§ 371 (c)(1),
(2) Date: Jan. 25, 2018

(87) PCT Pub. No.: WO2017/016540
PCT Pub. Date: Feb. 2, 2017

(65) Prior Publication Data
US 2018/0217098 A1   Aug. 2, 2018

(30) Foreign Application Priority Data
Jul. 28, 2015   (DE) .................. 10 2015 214 232

(51) Int. Cl.
*G01N 27/90* (2006.01)
*G01N 27/87* (2006.01)
*G01N 29/265* (2006.01)

(52) U.S. Cl.
CPC .......... *G01N 27/902* (2013.01); *G01N 27/87* (2013.01); *G01N 29/265* (2013.01)

(58) Field of Classification Search
CPC ..... G01N 27/902; G01N 27/87; G01N 29/265
(Continued)

(56) References Cited

U.S. PATENT DOCUMENTS 3,612,987 A    10/1971  Placke et al.
3,955,425 A *   5/1976  Corneau ................. B29C 47/92
                                                        73/622
(Continued)

FOREIGN PATENT DOCUMENTS

DE    3739190 A1    6/1989
DE    9108162 U1   12/1991
(Continued)

OTHER PUBLICATIONS

Brockett, Timothy; Rahmatsamii, Yahya: A Novel Portable Bipolar Near-Field Measurement System for Millimeter-Wave Antennas: Construction, Development, and Verification. In: IEEE Antennas and Propagation Magazine, vol. 50, 2008, No. 5, p. 121-130.

*Primary Examiner* — Nimeshkumar D Patel
*Assistant Examiner* — Jean F Morello
(74) *Attorney, Agent, or Firm* — Barlow, Josephs & Holmes, Ltd.

(57) ABSTRACT

A probe device for a rotating head of a rotary system comprises at least one support arm that is mounted so as to be rotatable about an axis of rotation, at least one probe that is connected to the support arm, and at least one cable guide for guiding a probe cable. The cable guide comprises a first end portion that extends along the support arm, from the probe to the axis of rotation, and a second end portion that originates essentially at the axis of rotation.

7 Claims, 2 Drawing Sheets

(58) Field of Classification Search
USPC .......................................................... 73/866.5
See application file for complete search history.

(56) References Cited

U.S. PATENT DOCUMENTS

| | | | | |
|---|---|---|---|---|
| 4,101,832 A * | 7/1978 | Baker | ................ | G01N 27/9093 |
| | | | | 324/227 |
| 4,297,636 A * | 10/1981 | Link | ................ | G01N 27/9033 |
| | | | | 324/240 |
| 4,500,749 A * | 2/1985 | Khoshnevis | ........... | G01B 7/004 |
| | | | | 178/19.01 |
| 5,517,114 A * | 5/1996 | Reitz | ................ | G01N 27/9013 |
| | | | | 324/232 |
| 6,785,973 B1 * | 9/2004 | Janssen | ................ | G01B 5/004 |
| | | | | 33/1 N |
| 7,242,186 B2 * | 7/2007 | Zimmermann | .... | G01N 27/9026 |
| | | | | 324/228 |
| 7,395,609 B2 * | 7/2008 | Powell | ................ | G01B 5/008 |
| | | | | 33/1 N |
| 9,625,286 B2 * | 4/2017 | Stanton | ................ | G01D 11/30 |
| 2011/0025316 A1 | 2/2011 | Faucher et al. | | |

FOREIGN PATENT DOCUMENTS

| | | |
|---|---|---|
| DE | 4324332 A1 | 1/1995 |
| DE | 10003782 A1 | 12/2001 |
| DE | 102012108241 A1 | 11/2013 |

\* cited by examiner

PROBE DEVICE, ROTATING HEAD, AND TEST APPARATUS

BACKGROUND OF THE INVENTION

The present invention relates to a probe device, which comprises at least one carrier arm mounted rotatably about a rotational axis, at least one probe connected to the carrier arm, and at least one cable guide for the guidance of a probe cable. The invention further relates to a rotating head having at least one such probe device and having at least one probe cable guided in the cable guide, and to a test apparatus having at least one such probe device or having at least one such rotating head.

In particular for the examination of semifinished products for faults, such as cracks and shrink holes, by means of eddy current or magnetic leakage flux methods, test apparatuses which are configured as rotating systems are employed. In such rotating systems, probe devices are disposed on rotatable rotating heads of the test apparatus. Since the rotating head, together with the probe devices disposed thereon, is rotated while an elongate test piece is pushed through a middle passage opening through the rotating head, the probe devices move relative to the test piece on a helical path. In order to be able to detect changes in the magnetic field resulting from flaws in the test piece, probes of the probe devices, which probes are intended for the eddy current method, must be located at a predefined distance, or as close as possible, to the surface of the test piece. In the magnetic leakage flux method, on the other hand, the probes are in contact with the test piece and drags on its surface.

A probe device or a probe carrier for a test apparatus, configured as a rotating system, for the non-destructive testing of an elongated test piece by means of leakage flux or eddy currents is known from DE 10 2012 108 241 A1. The probe carrier is of modular and plug-in design, so that the test apparatus can be rapidly adapted to a changed test piece diameter.

Other known probe devices have a carrier arm mounted such that it is freely movable about a pivot point. At one end of the carrier arm mounted in the manner of a two-sided lever is arranged the probe, and at that end of the carrier arm which lies opposite said first end is provided a counterweight. Insofar as a test piece moves for instance irregularly through the passage opening of the rotating head, the probes, owing to the rotatable mounting of the carrier arm that bears them, can take appropriate evasive action. By means of the counterweight and a spring that acts on the carrier arm, a position of the probe at a predefined distance from the surface of the test piece, and, where appropriate, a contact pressing force of the probe onto the test piece, given a predefined rotation speed of the rotating head and a predefined diameter of the test piece, can be adjusted.

In order that, in the case of large test pieces and correspondingly high rotation speeds of the rotating head, the probes do not lift off from the surface of the test piece, whereby the testing operation in the magnetic leakage flux method is interrupted, there is in practice a tendency to configure the spring force, and hence the contact pressing force of the probe onto the test piece, excessively high, or to reduce the rotation speed of the rotating head. A large contact pressing force leads, however, to increased wear of the probes dragging on the test piece surface, while a reduction of the rotation speed of the rotating head leads to a reduced throughput of the test piece. Also the correct adjustment of the distance of the probes from the surface of the test piece in the eddy current method generally proves difficult in practice, due to the influences of rotation speed and test piece diameter. A further influence is also exerted by probe cables, which run as cable bows or loops from a port or inlet on the rotating head to the probe device and, guided in a cable guide of said probe device via a carrier arm of the probe device, to the probe, in order to ensure the mobility of the carrier arm. Upon rotation of the rotating head, these cable bows experience a centrifugal force and thereby exert a torque on the carrier arm, whereby they influence the contact pressing force or the position of the probes in relation to the test piece.

SUMMARY OF THE INVENTION

The object of the present invention is therefore to provide a probe device, a rotating head and a test apparatus which simplify the adjustment of probes with respect to a test piece.

This object is achieved by the probe device, rotating head, and test apparatus of the present invention.

According to the invention, a probe device in which the cable guide has a first end portion running along the carrier arm from the probe to the rotational axis and a second end portion extending substantially from the rotational axis is proposed. In other words, both the first end portion and the second end portion bear substantially with one of their ends against the rotational axis, or one of their respective ends is positioned substantially on the rotational axis, or one of their respective ends is located level with the rotational axis. Both the first end portion and the second end portion hence form an angle with the rotational axis. This has the effect that a probe cable is led to the probe device or its probe, or led away therefrom, level with the rotational axis of the carrier arm. Consequently, the probe cable can produce no torque whatsoever on the carrier arm when both the probe device and the probe cable are rotated as part of a rotating head of a rotating system and experience a centrifugal force. Thus, nor can the probe cable in any way influence the adjustment of the position of the probe or exert the contact pressing force thereof on the surface of test pieces. The adjustment of the probe with respect to the test piece is thereby not only considerably simplified, a number of further advantages are also obtained. For instance, a lifting of the probe from the surface of the test piece is more effectively avoided, wherein the wear of the probe can also be reduced due to an optimal set contact pressing force. Maintenance intervals for the probe device are hereby extended. Insofar as the probe device possesses counterweights for adjusting the position of the probe or the contact pressing force thereof, reworking of these counterweights is no longer necessary. Required rotation speeds of the rotating head can always be achieved and thus enable maximum productivity. In case of collision with test pieces, the load on probe shoes resulting from easier evasion, even in contactless rotating systems, is reduced.

In general terms, the carrier arm can have a longitudinal axis, wherein the longitudinal axis and the rotational axis can be configured such that they are mutually skewed. The carrier arm or its longitudinal axis can also, however, intersect the rotational axis. In addition, the probe device can have more than one rotatably mounted carrier arm. For instance, the probe can be fastened to the ends of two or more parallelly arranged carrier arms, which are both mounted rotatably about the same rotational axis. Moreover, for the adjustment of the contact pressing force or the position of the probe, on the carrier arm can be arranged at least one counterweight, the position of which is advantageously adjustable along the carrier arm.

Embodiments of the probe device are possible in which the first end portion and the second end portion are directly connected to each other. In these cases, the two end portions substantially merge into each other at the pivot point of the carrier arm. In other embodiments of the probe device, a cable guide portion running along the rotational axis connects the first end portion and the second end portion one to the other. For instance, the first end portion can lead from the probe to the rotational axis or to the pivot point of the carrier arm, where it leads into the cable guide portion running parallel to the rotational axis, which cable guide portion in turn, along the rotational axis, leads away from the pivot point of the carrier arm and, remote from this, leads into the second end portion.

In the probe device according to the invention, the carrier arm can be mounted in the manner of a one-sided or a two-sided lever. In both cases, the probe, at one end or end portion of the carrier arm, can be connected to the same. If the carrier arm is mounted in the manner of a two-sided lever, then preferably, apart from the probe, at least one counterweight is fastened to the carrier arm, wherein probe and counterweight, with respect to the rotational axis of the carrier arm, are located on opposite sides, to be precise preferredly on opposite ends or end portions of the carrier arm.

Advantageously, a rotating head according to the invention has at least one spring, which acts with one end on the carrier arm of the probe device. Suitable selection of the point of action of the spring on the carrier arm, and of the spring constant thereof, can help to adjust the position of the probe relative to the test piece or to adjust the contact pressing force of the probe against the test piece.

A test apparatus according to the invention preferredly has at least one pair of probe devices, the probes of which are arranged facing each other. If a test piece is arranged or pushed through between the probes, then the probes can check two mutually opposite sides of the test piece simultaneously.

BRIEF DESCRIPTION OF THE DRAWINGS

The invention is explained in greater detail below with reference to drawings, wherein.

DESCRIPTION OF THE INVENTION

Figure 1:
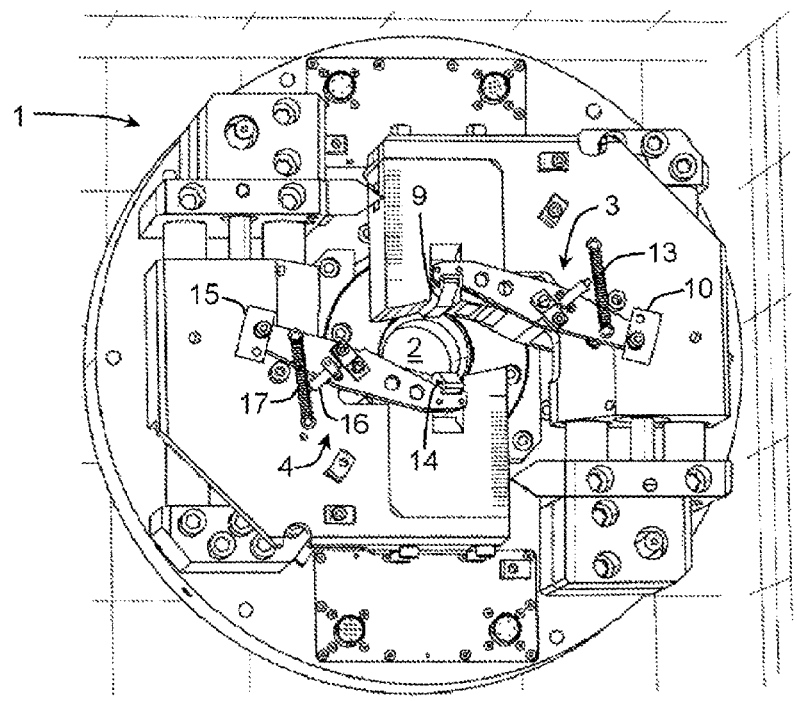
FIG. 1 shows a rotating head according to the prior art, comprising two probe devices.

In FIG. 1, a known circular rotating head 1 of a test apparatus configured as a rotating system is represented. The rotating head 1 has a central through hole 2 and two substantially identically configured probe devices 3 and 4.

Figure 2:
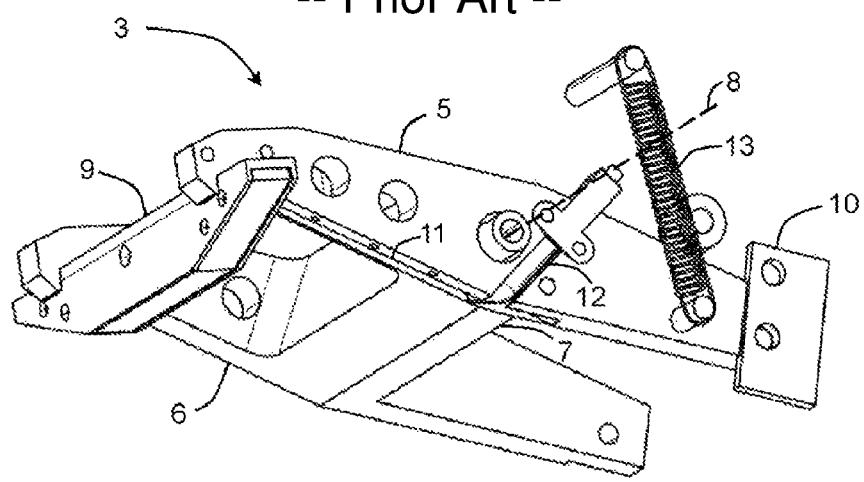
FIG. 2 shows a probe device according to the prior art.

The probe device 3 can be seen in FIG. 2 in enlarged representation. It comprises two elongate carrier arms 5 and 6, which are arranged parallel to each other and are connected to each other by means of a substantially centrally arranged middle web 7. Level with the middle web 7, the carrier arms 5 and 6 are mounted in the manner of a two-sided lever rotatably about a rotational axis 8 marked in dashed representation in FIG. 2. By those ends of the carrier arms 5 and 6 which are facing toward the through hole 2, a probe 9 extending between the carrier arms 5 and 6 is held, while, on that end of the carrier arm 5 which is facing away from the through hole 2, a counterweight 10 is arranged. In addition, the probe device 3 has a cable guide having a first end portion 11 extending from the probe 9 and running along the carrier arm 5, and a second end portion 12 adjoining the first end portion 11, wherein the second end portion 12 neither intersects the rotational axis 8 nor extends therefrom. The cable guide is provided to receive a probe cable (not represented in the figures for reasons of clarity). Finally, a spiral spring 13, at a point between the middle web 7 and the counterweight 10, acts on the carrier arm 5, hence on an end portion of the carrier arm 5, which end portion is facing away from the probe 9.

The probe device 4 corresponds in terms of its structure substantially to the probe device 3. In particular, the probe device 4 also has a probe 14, which is fastened to end portions of its carrier arms. At one end of a carrier arm of the probe device 4, which end lies opposite to the probe 14, a counterweight 15 is provided. From the spatial perspective of FIG. 1, of the cable guide of the probe device 4 only the second end portion 16 is visible. A spiral spring 17 acts with one end on an end portion of the carrier arm of the probe device 4, which end is facing away from the probe 14, at a point between the second end portion 16 of the cable guide and the counterweight 15 on the carrier arm.

In the rotating head 1, the two probe devices 3 and 4 are arranged such that their respective probes 9 and 14 lie substantially diametrically opposite each other in relation to the through hole 2.

During the operation of the test apparatus, an elongate test piece to be tested by the probes 9 and 14 is pushed through the through hole 2, while the rotating head 1 rotates about the test piece. Through suitable choice of the counterweights 10 and 15 of the probe devices 3 and 4 and of the spiral springs 13 and 17 acting on the probe devices 3 and 4, the distance which the probes 9 and 14 have to maintain, during the rotation of the rotating head 1, from the surface of the test piece, or the contact pressing force with which the probes 9 and 14 press onto the surface of the test piece, can be adjusted.

However, upon rotation of the rotating head 1, probe cables which are accommodated in the cable guides of the probe devices 3 and 4 and which, following exit from the second end portions 12 and 16 of said cable guides, run in an arc shape up to a port or inlet of the rotating head 1, experience centrifugal forces. These centrifugal forces in turn exert a leverage on the rotatably mounted probe devices 3 and 4, whereby the preset distance of the probes 9 and 14 from the surface of the test piece, or their contact pressing force onto the surface of the test piece, is influenced. Moreover, this influence is dependent on the respective rotation speed of the rotating head 1.

Figure 3:
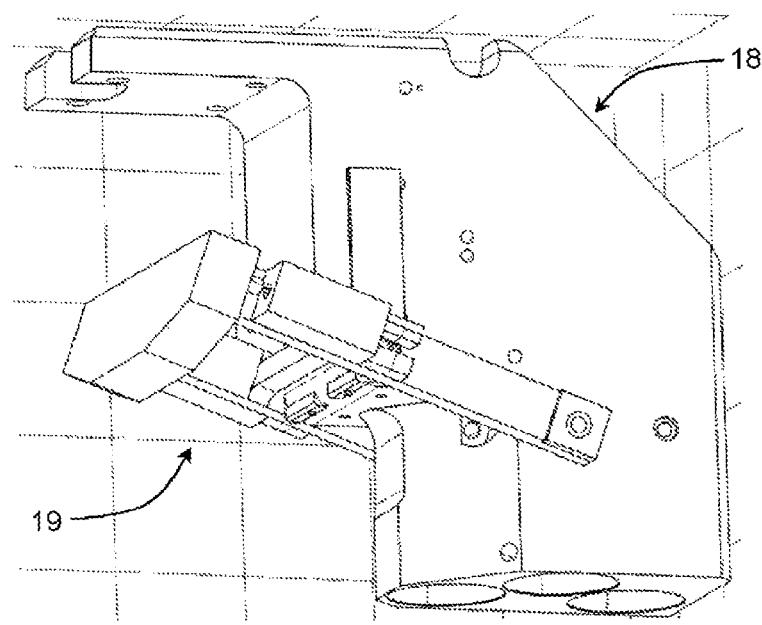
FIG. 3 shows a detailed view of a rotating head according to the invention.
Figure 4:
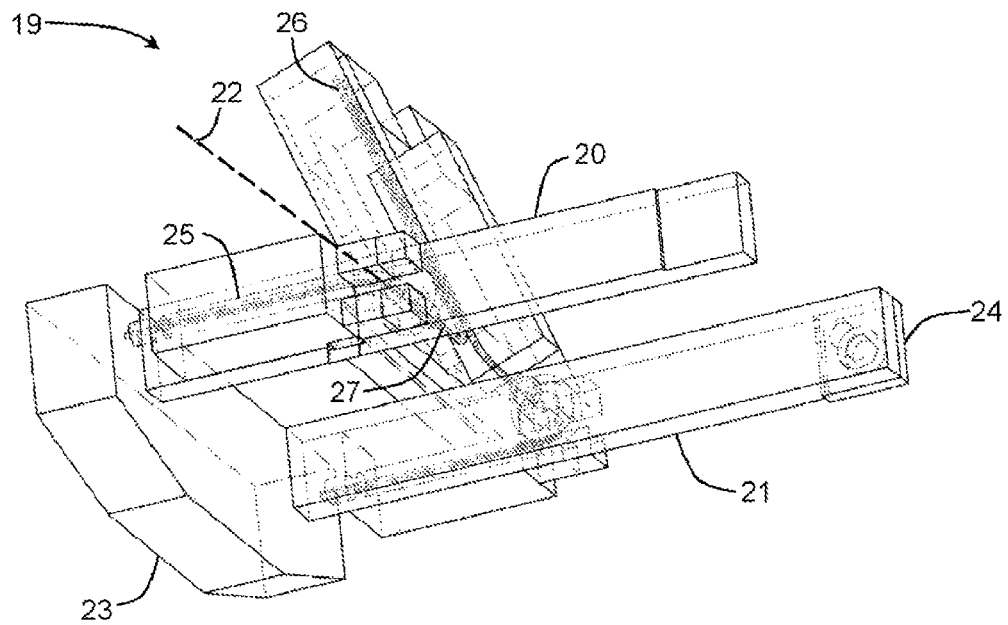
FIG. 4 shows a probe device according to the invention.

FIG. 3 now shows a detailed view of a rotating head 18 according to the invention, in which these problems have been overcome. This is down, above all, to its probe device 19 according to the invention, which in FIG. 4 is shown in enlarged representation. Similarly to the above-described known probe devices 3 and 4, the probe device 19 according to the invention also comprises two elongate carrier arms 20 and 21, which are arranged parallel to each other. Both carrier arms 20 and 21 are mounted in the manner of a two-sided lever rotatably about the same rotational axis 22, which in FIG. 4 is drawn in dashed representation. At one end of the carrier arms 20 and 21 a probe 23 is held extending between the carrier arms 20 and 21, while at the thereto opposite end of the carrier arm 21 a counterweight 24 is arranged. In the installed state of the probe device 19 in the rotating head 18, the probe 23 is facing toward the through hole (not visible in the detailed view of FIG. 3) of the rotating head 18. A second probe device, not shown in FIG. 3 and corresponding to the probe device 19, is provided in the rotating head 18 such that its respective probes, in relation to the through hole (not represented) of the rotating head 18, lie substantially diametrically opposite each other.

The probe device 19 according to the invention differs from the known probe devices 3 and 4 primarily by virtue of its cable guide for the reception of probe cables. For instance, the cable guide of the probe device 19 has a first end portion 25 running along the carrier arm 20 from the probe 23 to the rotational axis 22. A second end portion 26 extends substantially from the rotational axis 22 or forms an angle with this. The first end portion 25 and the second end portion 26 are connected by means of a cable guide portion 27, which, designed as a hollow shaft, runs along the rotational axis 22. In the installed state of the probe device 19 in the rotating head 18, the second end portion 26 is arranged fixedly or immovably relative to the rotating head 18, while the carrier arm 20 is rotatable about the rotational axis 22 and hence can execute a rotary motion relative to the second end portion 26. Within the hollow cable guide portion 27, a probe cable, when the carrier arm 20 is tilted, can twist flexibly without significantly changing its position or its distance relative to the rotational axis 22. On the carrier arm 21, a cable guide corresponding to the cable guide of the carrier arm 20 is provided.

Owing to the particular cable guide, having the first end portion 25 running up to the rotational axis 22, having the second end portion 26 extending from the rotational axis 22, and having the cable guide portion 27 parallel to the rotational axis 22, a probe cable (for reasons of clarity, not shown in FIGS. 3 and 4) can be guided such that, upon rotation of the rotating head 18, the influence of the centrifugal force on the probe device 19 according to the invention can be minimized. In particular, in the probe device 19 according to the invention, no cable bows whatsoever arise, which cable bows would be exposed to such a centrifugal force and would transmit this to the carrier arms 20 and 21. When, for example, the carrier arm 20 rotates about the rotational axis 22, the probe cable can twist freely within the hollow cable guide portion 27 without changing its shape or moving away from the rotational axis 22, so that nor can it exert any forces, resulting from the rotation of the rotating head 18, on the probe device 19. Hence the probe device 19 can be balanced, in accordance with the weight of the probe 23, once via the counterweight 24. The balanced probe device 19 then functions equally over the whole of the diameter range and rotation speed range of the rotating head 18. The contact pressing force against the test piece, or the distance of the probe 23 from the surface thereof, is generated only by a force independent from the centrifugal force, for example by torsion springs.

In another embodiment of a probe device according to the invention, a hollow cable guide portion is dispensed with and the first end portion is directly connected to the second end portion.

The invention claimed is:

1. A probe device, comprising:
at least one carrier arm mounted rotatably about a rotational axis,
at least one probe connected to the at least one carrier arm, and
at least one cable guide for the guidance of a probe cable, wherein
the at least one cable guide has a first end portion running along the at least one carrier arm from the at least one probe to the rotational axis and a second end portion extending from the rotational axis,
wherein at least a portion of the probe cable extends parallel to the rotational axis.

2. The probe device as claimed in claim 1, wherein a cable guide portion running along the rotational axis connects the first end portion and the second end portion one to the other.

3. The probe device as claimed in claim 1, wherein the at least one carrier arm is mounted in a configuration of a one-sided or a two-sided lever.

4. The probe device as claimed in claim 1, wherein the probe device is configured and arranged in a rotating head and having at least one probe cable guided in the at least one cable guide.

5. The probe device as claimed in claim 4, wherein the probe device is configured and arranged in a test apparatus or the at least one rotating head is configured and arranged in the test apparatus.

6. The probe device as claimed in claim 5, having at least one pair of probe devices, wherein the probes of which are arranged facing each other.

7. The probe device of claim 1, wherein the probe cable does not apply forces on the probe device as a result of rotation of the probe device.

* * * * *